United States Patent [19]

Moister, Jr.

[11] 3,935,508

[45] Jan. 27, 1976

[54] HIGH VOLTAGE DISCHARGE SWITCH FOR PROTECTING SENSITIVE ELECTRONIC EQUIPMENT AND THE OPERATORS THEREOF

[75] Inventor: Douglas E. Moister, Jr., Plymouth, Mich.

[73] Assignee: Burroughs Corporation, Detroit, Mich.

[22] Filed: Aug. 5, 1974

[21] Appl. No.: 494,978

[52] U.S. Cl. ............ 317/2 R; 200/144 AP; 317/2 B

[51] Int. Cl.$^2$ ........................ A61N 1/14; H05F 3/04

[58] Field of Search ............ 317/2 R, 2 B; 174/5 R, 174/5 SG, 5 SB, 6; 200/51.09, 144 AP; 307/202, 94, 98; 338/215, 334

[56] References Cited

UNITED STATES PATENTS

| | | | |
|---|---|---|---|
| 3,099,774 | 7/1963 | Crane | 317/2 R |
| 3,577,208 | 5/1971 | Petrick | 317/2 R |
| 3,621,164 | 11/1971 | Backer | 317/2 R |
| 3,780,345 | 12/1973 | Earman, Jr. | 317/2 B |

OTHER PUBLICATIONS

IBM Technical Disclosure Bulletin, Vol. 15, No. 7, (Dec. 1972), pp. 2200–2201, "Protection Against Electrostatic Noise."

*Primary Examiner*—J. D. Miller
*Assistant Examiner*—Harry E. Moose, Jr.
*Attorney, Agent, or Firm*—Charles P. Padgett, Jr.; Edwin W. Uren; Paul W. Fish

[57] ABSTRACT

A method and apparatus for protecting the sensitive electronic or magnetic circuitry of modern business machines, mini-computers, and the like, while preventing the operator thereof from experiencing any discomfort. A high voltage discharge switch attachable to such a machine is used to discharge an accumulated charge of static electricity from the machine operator's body in approximately one tenth of a second without causing any discomfort. The high voltage switch employs an upper finger touch contact having a sharp point which, when depressed by the machine operator, comes into close proximity with a lower contact which is coupled through a resistive means to the frame of the machine and causes a corona discharge from the sharp point which initiates the transfer of at least a portion of the stored electrostatic charge prior to actual contact between the sharp point and the lower contact such that the transferred electrostatic charge is effectively dissipated through the resistive means without the usual spark-gap-type shock-producing discharge which usually results when actual contact is made thereby avoiding any discomfort to the machine operator and avoiding spurious signals which could produce errors in the state of sensitive logic circuits, memories or the like.

12 Claims, 3 Drawing Figures

HIGH VOLTAGE DISCHARGE SWITCH FOR PROTECTING SENSITIVE ELECTRONIC EQUIPMENT AND THE OPERATORS THEREOF

BACKGROUND OF THE INVENTION

This invention relates to a method and apparatus for protecting sensitive electronic or magnetic memories, logic circuitry, and the like in modern business machines or computer equipment from destruction, disruption or errors which could result from spurious impulses generated by an electrostatic discharge from the equipment operator's body to the equipment while simultaneously insuring that the equipment operator does not experience a harmful or annoying electrical shock.

Most persons have probably noted that a charge of static electricity may be generated by a person walking across a floor covered by carpeting made of certain synthetic materials, or when wearing clothing manufactured of certain synthetic fibers. Under conditions of relatively low humidity, a relatively large electrical potential may be developed, and when the person extends his fingers or hands while attempting to touch an object at a lower electrical potential, current flows from the extremeties thereof causing the person to experience a shocking sensation. Although the shock experienced is often more annoying than harmful, it is desirable to provide devices for eliminating the shock.

Several attempts have been made in the prior art for minimizing the shock experienced by such a person. Most of the attempts have employed discharging devices which can be used in conjunction with doorknobs, switches, push buttons and the like which can operate to discharge the accumulated charge of static electricity stored on the person's body without substantial discomfort to the charged person. U.S. Pat. No. 3,621,164 to Stanley Backer, and U.S. Pat. No. 3,099,774 to John J. Crane are examples of such prior art systems and usually employ a means for dissipating the charge via a spark discharge across an air gap or through a resistor. U.S. Pat. No. 3,780,345 to Ernest Earman, Jr. provides a static electricity de-shocker which employs a 10 megaohm resistor to intercept, arrest or reduce the static discharge to a non-shocking state or degree.

All of the systems of the prior art are aimed primarily at reducing the shock experienced by the persons who have accumulated the static charge. Such systems employ a spark discharge across an air gap or a direct contact discharge through a high valued resistor. None of these systems completely eliminate discomfort to the charged person and none of these prior art systems serve to protect anything other than the charged person.

Many of today's modern business machines, minicomputers, computer terminals, computers and the like, contain sensitive electronic and/or magnetic circuits and/or memories. A static discharge which could result if the machine operator's body was at a substantially different electrical potential from that of the machine were to make contact or near contact with the machine could produce a spurious signal which could change the state of various logic circuits or the contents of various electronic or magnetic memories so as to cause errors in the machine's operation or otherwise damage the machine itself.

SUMMARY OF THE INVENTION

In view of these problems, it is an object of this invention to provide a method and apparatus for preventing the disruption of sensitive electronic and/or magnetic circuits or memories which may result from a static discharge between an operator who has accumulated a charge of static electricity and a machine housing such circuitry or memories.

It is another object of this invention to provide a method and apparatus for discharging the electrostatic potential stored by a human body in such a manner so as to eliminate any discomfort to the human body.

It is a further object of this invention to provide a high voltage discharge switch which may be used to discharge the body of a human operator in approximately one tenth of a second without causing any discomfort to the human operator while simultaneously insuring that the sensitive electronic and/or magnetic circuits or memory of the machine upon which the human operates is in no way disrupted.

It is still a further object of this invention to provide a high voltage discharge switch which employs an upper contact having a sharp contact point such that when the upper contact is depressed and comes into reasonably close proximity to a lower contact, the electrostatic charge applied to the upper contact is at least partially transferred via a corona discharge from the point contact before being dissipated through resistive means coupling the lower contact to ground.

It is yet a further object of this invention to protect both sophisticated electronic machinery and the machine operators thereof by providing said machinery with a discharge switch which can be used to dissipate the charge stored on the human operator by means of a corona discharge without harming either the human operator or the electronic machinery.

Accordingly, this invention protects both the sophisticated electronic and/or magnetic circuitry or memories associated with many of today's modern business machines, mini-computers and the like and the humans who operate such machines by providing the machine with a high voltage electrostatic discharge switch which is capable of discharging a human body in approximately one tenth of a second without causing any discomfort to the human operator or harm to the sophisticated machinery. The high voltage discharge switch employs a point contact which produces a corona discharge when in the operative position thereby eliminating harmful spark-gap shock-producing type discharges heretofore employed in the prior art and insuring a safe, rapid discharge of the human operator while eliminating any possibility of harming a component of the machines or producing errors in the operation thereof.

BRIEF DESCRIPTION OF THE DRAWINGS

Other objects, advantages and features of this invention will become more fully apparent from the following detailed description, appended claims, and accompanying drawings in which like reference numerals designate corresponding parts:

DETAILED DESCRIPTION OF THE DRAWINGS

Figure 1:
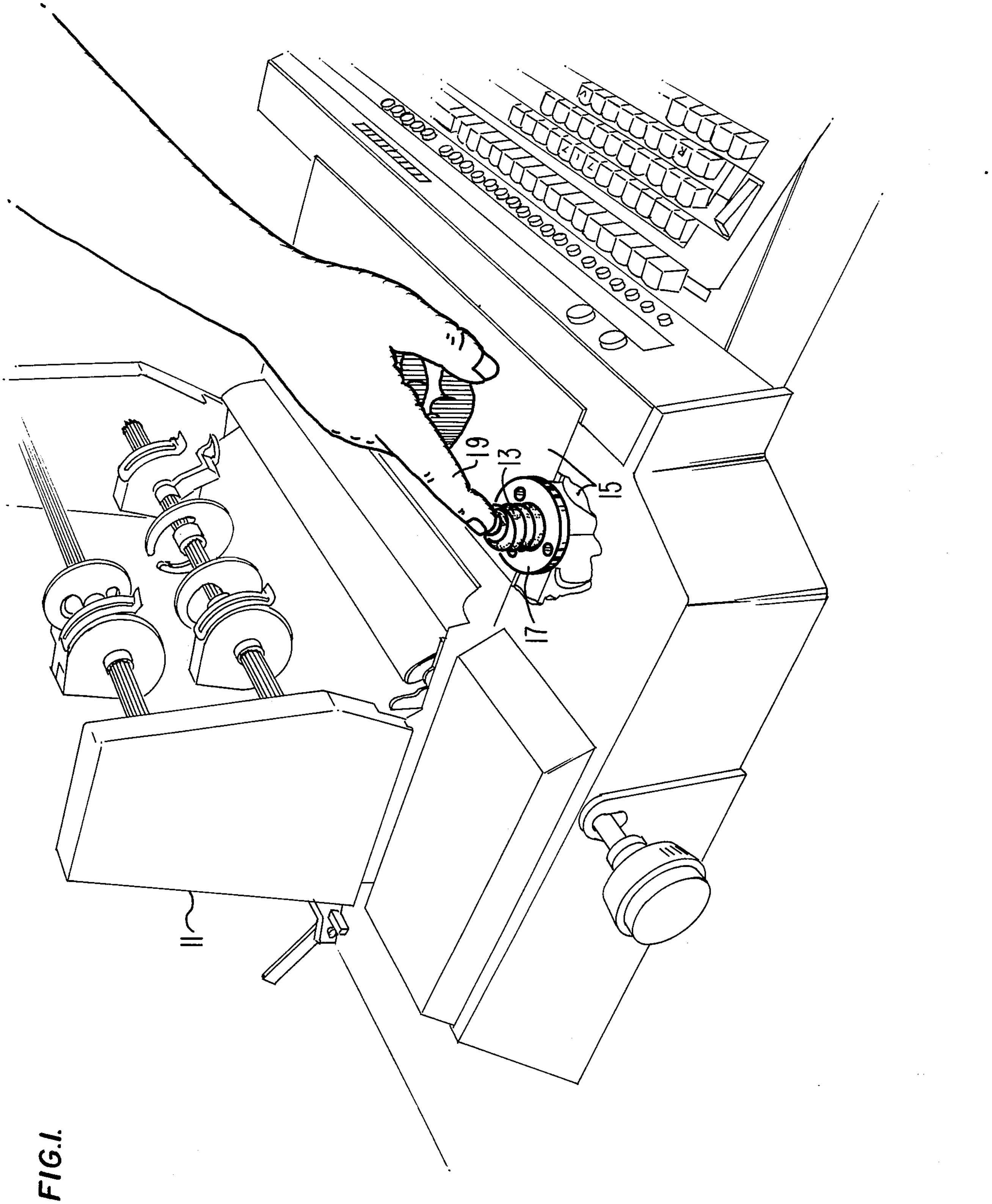
FIG. 1 is an overall perspective view of a sophisticated modern business machine employing the high voltage discharge switch of the present invention.

FIG. 1 illustrates a modern business machine 11 which contains sophisticated electronic and/or magnetic circuits or memory. Typically, the business machine could, for example, be a Burroughs Series L or TC type machine such as the L8000, a description of which can be found in Burroughs *L8000 MINI-COMPUTER Technical Manual* which was copyrighted in January 1973 and is incorporated by reference into this description. The high voltage electronic discharge switch 13 of the present invention is shown as being connected to the chassis or frame 15 of the machine 11 via screws, threaded bolts, or other fastening means which connect the base 17 of the discharge switch 13 securely to the frame 15 of the machine 11. FIG. 1 shows a finger 19 of a human operator in the act of depressing the high voltage discharge switch 13 so as to discharge the electrostatic potential stored on the human operator's body so as to protect the machine while simultaneously insuring that the operator does not experience any discomfort due to electrical shock.

Figure 2:
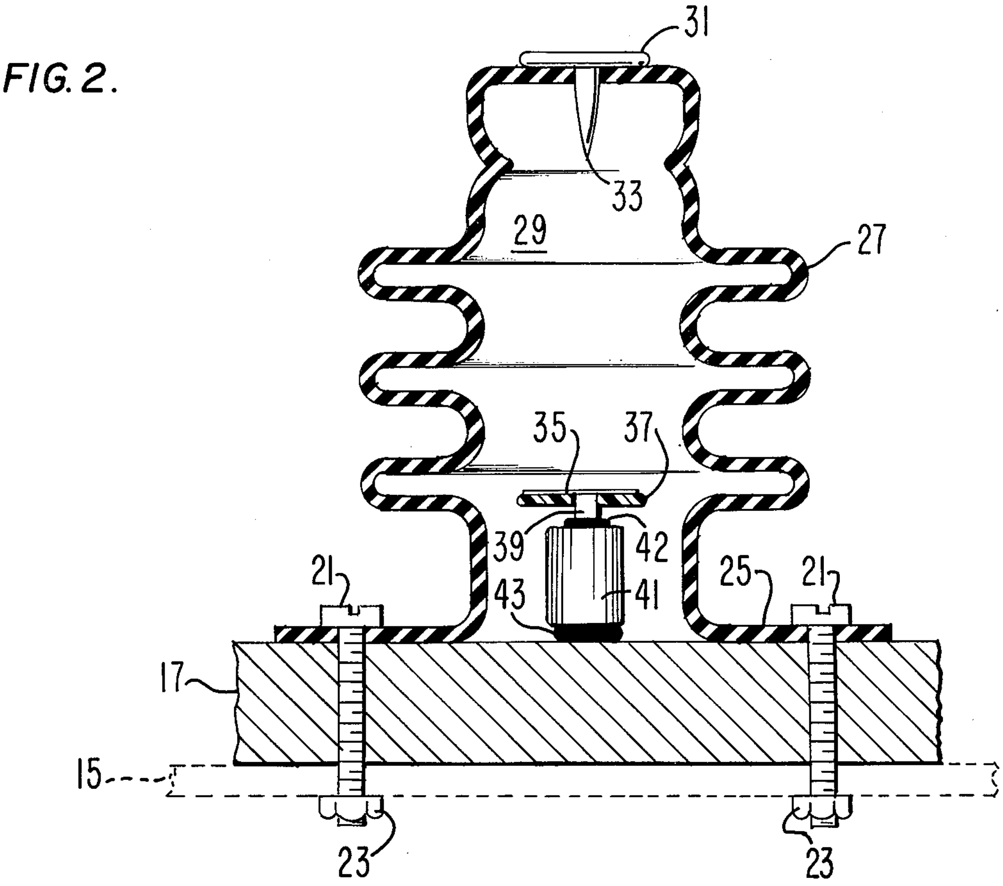
FIG. 2 is a sectional view of the high voltage discharge switch of the present invention in its normal non-operative position.

FIG. 2 illustrates a sectional view of the high voltage discharge switch 13 of the present invention. The base 17 of the switch is secured to the frame 15 by threaded bolt 21 and nut 23. The bolt and nut combination also secures the base portion 25 of the thin rubber housing or nipple 27 to the base 17.

In the prime embodiment disclosed herein the nipple or boot structure 27 is shaped so as to form a central bounded cavity or air space 29 having an open portion at the lower end thereof which is exposed to the base 17 and which is bounded by the wall of thin rubber material which forms the base portion 25 of the nipple 27. The closed upper end of nipple 27 which provides the upper boundary of the confined air space houses an upper contact 31 which may be a thumbtack or the like which pierces the thin rubber wall at the top of nipple 27 and has its sharp pointed end 33 extending into the upper portion of air space 29 while its smooth upper surface which is adapted for finger touch contact by the human operator remains above the top of the nipple and is external to the confined air space. A lower contact is housed in the lower portion of the air space 29 and is comprised of an electrically conductive material 35 such as copper or the like deposited on a printed circuit board 37 or similar structure so as to form a lower contact. The electrically conductive contact material 35 is connected through the printed circuit board structure 37 via a plated-through hole 39 or the like through a 3 megaohm resistor 41 at a contact point 42 comprising solder or the like and the opposite end of resistor 41 is connected to the base 17 at point 43 via solder or the like such that an electrically conductive path is provided between the contact material 35 of the top portion of the lower contact and ground as represented by frame 15 of the machine 11 via a continuous path comprising the plated hole 39, contact point 42, resistor 41, contact point 43 and the base 17 of the switch which is securely fastened to ground via frame 15.

Figure 3:
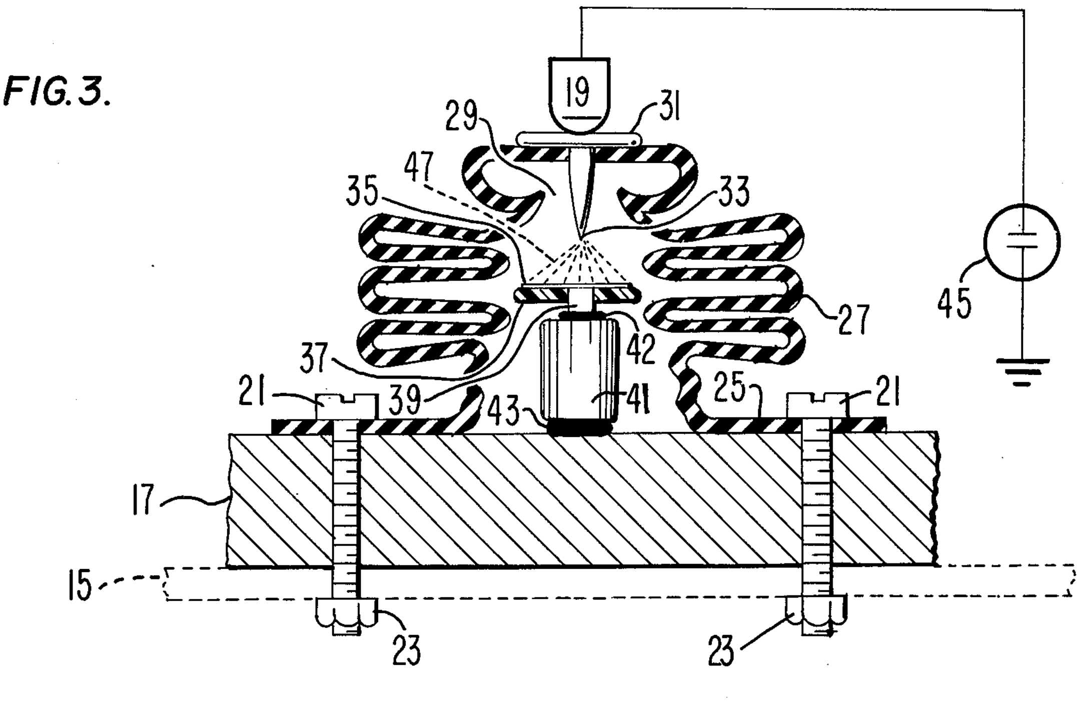
FIG. 3 is a sectional view of the high voltage discharge switch of the present invention in its depressed or operative position.

FIG. 3 illustrates the high voltage discharge switch of the present invention in the operative or discharging position. A human body is represented by a capacitor 45 which may have a capacitance, for example, in the 100 to 180 pico-farad range. One end of the human body or capacitor 45 is connected to ground and the other terminates in finger 19. As the finger 19 makes contact with upper contact 31 and compresses the thin rubber nipple 27, the length of the air gap between the sharp point 33 of the upper contact and the electrically conductive coating 35 of the upper layer of the printed circuit board 37 of the lower contact is variably reduced to a point at which a corona discharge, illustrated by dotted lines 47, occurs. The corona discharge effectively transfers at least a portion of the original accumulated charge of static electricity prior to any actual contact or arcing between sharp point 33 and conductive coating 35 which effectively dissipates any remaining portion of the transferred charge through the path comprising contact 35, connector 39, contact point 42, resistor 41, contact point 43 and base 17 to ground as represented by the frame 15 without causing any discomfort to the human body and without disturbing in any manner the sophisticated electronics or magnetics of machine 11. The initial partial transfer via the corona discharge insures an absolute minimum of shock and produces a system far superior to any heretofor known in the art.

With this detailed description of the structure and operation of the present invention, it will be obvious to those skilled in the art that various modifications can be made without departing from the spirit and scope of the invention which is limited only by the appended claims.

I claim:

1. A device for transferring an accumulated charge of static electricity between a person and an object such that the person does not experience any discomfort due to electrical shock, said device comprising:

upper contact means having an upper finger touch contact surface for receiving an accumulated charge of static electricity from said person;

lower contact means for effectively dissipating a transferred charge without causing any discomfort to said person;

flexible housing means for defining an air space and establishing an initial distance between said upper contact means and said lower contact means, said flexible housing means being responsive to the pressure exerted when said person touches said upper contact surface for variably reducing said distance; and wherein said upper contact means further includes a sharp pointed means responsive to said established distance having been reduced to a first length for initiating a corona discharge to initially transfer at least a portion of said accumulated charge of static electricity, said sharp pointed means being responsive to said established distance having been further reduced to a second length for directly transferring any remaining portion of said accumulated charge of static electricity to said lower contact means.

2. The device of claim 1 wherein said lower contact means includes:

an electrically conductive surface means for receiving the transferred charge;

resistive means for effectively dissipating said charge transferred to said conductive surface;

means for coupling said electrically conductive surface means to said resistive means; and means for coupling said resistive means to said object.

3. The device of claim 2 wherein said electrically conductive surface means includes a dielectric printed circuit board having a copper coating on the top portion thereof and wherein said means for connecting said electrically conductive surface means to said resistive means includes a plated-through hole in said printed circuit board electrically connecting said copper coating to said resistive means.

4. The device of claim 3 wherein said resistive means includes a resistor having a value of less than 10 megaohms.

5. The device of claim 1 wherein said flexible housing means includes:

an upper portion of thin flexible material adapted for positioning said upper contact means such that said contact surface is external to said defined air space while said sharp pointed means extends through said thin flexible portion and into said defined air space;

a lower portion of thin flexible material having a flanged lip for coupling said lower portion to said object, the walls of said lower portion being shaped for forming a cavity at the lower limit to said defined air space for housing said lower contact means; and a flexible middle portion for variably reducing the distance between said sharp pointed means and said electrically conductive surface means, said thin middle portion being variably contractable in response to finger touch pressure exerted on said upper finger touch contact surface for reducing said distance.

6. In an electronic business machine having sensitive electronic circuitry therein, which circuitry can be harmed or caused to provide erroneous signals in response to a spurious impulse generated by an electrostatic discharge such as may occur when an operator of said business machine who has accumulated a charge of static electricity makes contact with said machine, the improvement comprising:

contact means having a first surface adapted for finger-touch contact by said operator and another surface terminating in a sharp point;

resistive means for effectively dissipating any accumulated charge of static electricity transferred thereto; and housing means for defining a variable space, and housing means having an upper portion including means for positioning said contact means such that said first surface is external to said defined space and said sharp point penetrates to within the top of said defined space, a lower portion having means for housing said resistive means, and a variable middle portion comprising means for normally maintaining a predetermined distance between said sharp point and said resistive means so as to prevent a corona discharge from said sharp point and responsive to the operator's application of finger touch pressure to said first surface for reducibly varying said predetermined distance so as to initiate a corona discharge from said sharp point at a first reduced distance so as to effect at least a partial transfer of said accumulated charge from said operator without discomfort to said operator and for further reducibly varying said distance until any remaining portion of said accumulated charge is directly transferred to said resistive means.

7. The improved electronic business machine of claim 6 wherein said housing means includes a thin flexible nipple-like body comprising said upper portion, said lower portion, and said middle portion and wherein said resistive means includes a resistor, means for coupling one end of said resistor to said business machine, and means for coupling the other end of said resistor to an electrically conductive means for receiving the charge transferred by said sharp point.

8. The device of claim 6 wherein said contact means includes a thumbtack-like structure, said first surface adapted for finger touch contact comprising the head of said thumbtack-like structure and said sharp pointed means comprising the pointed tip of said thumbtack-like means, and wherein said resistor has a value of less than 10 megaohms.

9. In an apparatus for preventing a harmful discharge of static electricity such as may occur whenever a person who has accumulated a charge of static electricity touches an object which is at a different electrical potential, said apparatus including an electrical contact for receiving the accumulated charge of static electricity from said person and a resistive means for effectively dissipating any charge transferred thereto, a method of minimizing discomfort to said person while insuring a complete transfer of the accumulated charge, said method comprising the steps of:

providing said electrical contact with a means for facilitating a corona discharge;

spacing said means for facilitating said corona discharge a predetermined distance from said resistive means;

reducing said distance to initiate said corona discharge and transfer at least a portion of said accumulated charge from said electrical contact; and further reducing said distance unitl any remaining portion of said accumulated charge is transferred to said resistive means.

10. An apparatus for discharging an accumulated charge of static electricity from a human body without discomfort to said human body comprising:

means for contacting said human body;

means coupled to said contacting means and responsive to said accumulated charge of static electricity for initiating a corona discharge to transfer at least a portion of said accumulated charge; and resistive means for effectively dissipating any charge transferred thereto.

11. The discharging apparatus of claim 10 wherein said means for contacting said human body includes an electrically conductive charge-receiving means and wherein said means coupled to said contacting means for initiating a corona discharge to transfer at least the portion of said accumulated charge includes an elongated electrically conductive member having one end coupled into electrical contact with said electrically conductive charge-receiving means and its opposite end terminating in a sharp point for facilitating said corona discharge.

12. The discharging apparatus of claim 11 further including a housing means having a first end portion for housing said resistive means; a second end portion for positioning said contacting means such that said electrically conductive charge-receiving means is positioned external to said second end such that the sharp pointed end of said elongated member for facilitating a corona discharge extends through said second end of said housing means; and a central portion coupling said first end of said second end for normally biasing the sharp pointed end of said elongated member for facilitating the corona discharge a first distance away from said resistive means and responsive to the pressure exerted when said human body contacts said contacting means for reducing said first distance and initiating a corona discharge before said sharp pointed end of said elongated member contacts said resistive means for dissipating at least a portion of said accumulated charge without discomfort to said human body and responsive to further pressure for bringing said sharp pointed end into contact with said resistive means for dissipating any remaining charge.

* * * * *